US005972347A

United States Patent [19]
Eder et al.

[11] Patent Number: 5,972,347
[45] Date of Patent: *Oct. 26, 1999

[54] PHARMACEUTICAL COMPOSITION CONTAINING A NEUTRALIZED VIRUS AND USE THEREOF

[75] Inventors: Gerald Eder, Rekawinkel; Johann Eibl, Vienna, both of Austria

[73] Assignee: Baxter Aktiengesellschaft, Vienna, Austria

[*] Notice: This patent issued on a continued prosecution application filed under 37 CFR 1.53(d), and is subject to the twenty year patent term provisions of 35 U.S.C. 154(a)(2).

[21] Appl. No.: 08/702,123

[22] Filed: Aug. 23, 1996

[30] Foreign Application Priority Data

Aug. 24, 1995 [DE] Germany .................. 195 31 226

[51] Int. Cl.$^6$ .................. A61K 39/29; A61K 39/00; A61K 39/12; A61K 39/42
[52] U.S. Cl. .................. 424/228.1; 424/134.1; 424/147.1; 424/149.1; 424/184.1; 424/199.1; 424/204.1
[58] Field of Search .................. 424/199.1, 204.1, 424/184.1, 134.1, 149.1, 147.1, 228.1

[56] References Cited

U.S. PATENT DOCUMENTS 4,493,825  1/1985  Platt et al. .................. 424/88

FOREIGN PATENT DOCUMENTS 9104750  4/1991  WIPO .................. A61K 39/42

OTHER PUBLICATIONS

Shimizu et al., J. Virol. 68(3):1194–1500, 1994.
André et al. "Inactivated Candidate Vaccines for Hepatitis A" In: Progress in Medical Virol., Melnick, Ed., Basel, Karger, 1990, vol. 37,pp. 72–95.
Hedenström et al., Vaccine, 13(8): 759–762, 1995.
Jilg, Wolgang et al. "Hepatitis A Vaccine" In: Vaccines, 2$^{nd}$ Edit., Plotkin & Mortimer, Eds. W.B. Saunders Comp., Philadelphia, pp. 583–595, 1994.
Miriam Alter, Archives of Pathology and Laboratory Medicine 118(4):342–345, 1994.
Zuckerman et al., J. Hepatology, 22(Suppl. 1): 97–100, 1995.
Haynes, Science, 260: 1279–1286, 1993.
Emini, E.A. Aids Vaccine Research & Clinical Trials. Putney SD & Bulognesi DP, Eds. New York, Marcel Dekker pp. 369–378, 1990.
Spichtin et al., "Ultrastructural Alterations In Hepastocytes And Sinus Endothelia In Expeimental Non–A, Non–B Hepatitis In Chimpanzee With And Without Immunoglobulin Prophylaxis", *journal of Medical Virology*, vol. 12:215–226, (1983).
Eder et al., "Transmission of Non–A, Non–B Hepatitis to Chimpanzees: A Second and Third Episode Caused by the Same Inoculum", *Viral Hepatitis and Liver Disease*, pp. 550–552, (1988).
Leibl et al., "Multiple Infusions of Human Intravenous Immunoglobulin in Chimpanzees Do Not Lead to Immune Elimination", *Clin. exp. Immunol.*, vol. 81:454–458, (1990).
Prince et al., "Immunity in Hepatitis C Infection", *The Journal of Infectious Diseases*, Vlo. 165:438–443, (1992).
Farci et al., "Lack of Protective Immunity Against Reinfection with Hepatitis C Virus", *Science*, vol. 258:135–140, (1992).
Gollins et al., "A New Mechanism for the Neutralization of Enveloped Viruses by Antiviral Antibody", *Nature*, vol. 321:244–246, (1986).
Hedenstroem et al., "Vaccination Against Tick–borne Encephalits (TBE): Influence of Simultaneous Application of TBE Immunoglobulin on Seroconversion and Rate of Adverse Events", *Vaccine*, vol. 13(6):750–762, (1995).
Tabor et al., "Primate Animal Models and Titered Inocula for the Study of Human Hepatitis" *J. Med. Primatol.*, vol. 12:305–318, (1983).
Guidelines of the German Pharmacopia DAB 10 (3rd supplement 1994) "Immunglobulin vom Menschen Zur Intravenoesen Anwendung".
Eder et al., "Safety Testing of Blood Products in Chimpanzees", *Symp. Vienna*,pp. 156–165, (1994).
Thefeld et al., "Reference Values for the Determination of GOT, GPT, and Alkaline Phosphatase in Serum With Optimal Standard Methods", *Dtsch. Med. Wschr.*, vol. 994:343–351, (1974).
Lehrbuch et al., "Synopsis Der Leberkrankheiten", *Thieme Verlag Stuttgart*, Table of Contents, (1974).
Schmidt et al., "Clinical Pathology of Viral Hepatitis", *Laboratory and Clinical Science*, pp. 411–487, (1983).
Klin. Gastroenterologie in 2 Baenden, Thieme Verlag, Stuttgart (1984), Laboruntersuchungen, Chapter by Wuest.
Rosalki et al., "Serum γ–Glutamyl Transpeptidase Activity in Alcoholism", *Clin. Chem. Acta*, vol. 39:41–47, (1972).
Rosalki, "Gamma–Glutamyl Transpeptidase", *Chem. Chem.*, vol. 7:53–107, (1975).
Valcnza et al., "The Clinical Chemistry of Chimpanzees", *J. Med. Primatol.*, vol. 14:350–315, (1985).
Weill et al., "The Predictive Value of Gamma–Glutamyl Transferase and Other Peripheral Markers in the Schreening of Alcohol Abuse", *Advances in Biomedical Pharmacology*, 3rd Series, Masson, Paris, pp. 195–198, (1982).

(List continued on next page.)

*Primary Examiner*—Chris Eisenschenk
*Assistant Examiner*—Mary K Zeman
*Attorney, Agent, or Firm*—Foley & Lardner

[57] ABSTRACT

The invention relates to a pharmaceutical composition for prophylactic and/or therapeutic treatment of patients for immunization against a virus infection and is characterized in that this is obtainable by neutralizing the enriched and/or purified virus with antibodies. The invention further comprises a kit for the production of this composition as well as the use of a virus neutralized with antibodies for the production of a pharmaceutical composition.

9 Claims, No Drawings

OTHER PUBLICATIONS

Persijn et al., "A New Method for the Determination of γ–Glutamyltransferase in Serum", *J. Clin. Chem. Clin. Biochem.*, vol. 14(9):421–427, (1976).

Ishak et al., "Histological Grading and Staging of Chronic Hepatitis", *Journal of Hepatology*, vol. 22:696–699, (1995).

Pfeifer et al., "Experimental Non–A, Non–B Hepatitis: Four Types of Cytoplasmic Alteration in Hepatocytes of Infected Chipanzees", *Virchows Arch. B Cell Path.*, vol. 33:233–243, (1980).

Schaff et al., "Ultrastructural Alterations in Serial Liver Biopsy SpeicmensFrom Chimpanzees Experimentally Infected with a Human Non–A, Non–B Hepatitis Agent", *Virchows Arch [Cell Pathol]*, vol. 45:301–312, (1984).

Schaff, "Intracytoplasmic Crystalline Inclusions in the Hepatocytes of Humans and Chimpanzees", *Ultrastructural Pathology,* vol. 14:303–309, (1990).

Shimizu et al. J. Virol. 68(3): 1494–1500, Mar. 1994.

Jilg et al. "Hepatitis A Vaccines", In: Vaccines 2nd Edition, Plotkin et al. eds., W.B Saunders Company, Philadelphia, pp. 583–595, 1994.

Randall et al. Vaccine 12(4): 351–358, 1994.

Celis et al. Science 224:297–299, 1984.

Hedenstrom et al. Vaccine 13(8): 759–762, 1995.

Marusic–Galesic et al. Immunology 72: 526–531, 1991.

Miriam Alter Archives of Pathology and Laboratory Medicine 118(4):342–345, 1994.

Zuckerman et al. J. Hepatology 22(Suppl. 1:97–100, 1995.

Haynes et al. Science vol. 260: 1279–1286, 1993.

Cruse & Lewis, Illustrated Dictionary of Immunology, CRC Press, Inc., New York, p. 73, 1993.

Arvies et al. Immunology 65: 229–235, 1988.

PHARMACEUTICAL COMPOSITION CONTAINING A NEUTRALIZED VIRUS AND USE THEREOF

The present invention relates to pharmaceutical compositions which contain the combination of a virus with a neutralizing antibody as well as the use thereof.

The recognition that a previous exposure to small amounts of a pathogen or a fragment thereof can afford subsequent protection against a serious illness has made it possible to prevent major viral diseases such as pox, yellow fever, rabies, polio, measles and mumps. Vaccines directed against viruses have demonstrated dramatic success, especially in view of the shortage of anti-viral drugs.

Several clearly defined modes for developing a vaccine are available. There are viruses different from the target virus which can be used to stimulate the immune system but do not cause any serious disease themselves. This way was chosen in the fight against pox or cowpox pathogen. However, viruses can also be artificially modified in such a manner that their ability to cause a serious disease is lost, but not their antigen conformation necessary to stimulate the immune system. Such attenuated (weakened), living viruses are presently employed in vaccines against measles, polio, mumps and rubella.

A further mode is afforded by killing the corresponding virus before its use as a vaccine. Here, the required antigens must remain intact despite the loss of the replicability and pathogenicity. The disadvantage of these dead vaccines with respect to live vaccines lies in the fact that their immunization effect is weaker, and therefore, they have to be administered in regular intervals in order to guarantee effective protection.

Assuming that the vaccination sucess is determined by the presence of viral antigens alone which are found on fragments of the virus, it is then understandable that vaccines can also be produced from virus fragments or purified viral proteins. Above all, the latter method should find wide application in the future, because it is possible today to gene-technologically produce the desired antigens in a simple manner and in sufficient amounts. This method is currently being tested to obtain protection against hepatitis, herpes and AIDS viruses.

Independent of the method of virus production, the desired properties are always the same. Obviously, the virus must effectively stimulate the immune system in order to induce an impunity in this manner which is as long-lived as possible. Additionally, the vaccines cannot hive any serious side effects; and for world wide use, the vaccine should be inexpensive and stable over a long period of time.

A difficulty in modern virus production is that various vaccines only cause insufficient immunity due to a high mutation rate of the viruses. In such cases, it is necessary to look for methods of vaccine production which cause a higher immunity in the host, and therewith, are capable of effectively protecting the host against the pathogen.

It is state of the art that when chimpanzees are inoculated with an infectious Factor VIII preparation, and in addition, a human immunoglobulin preparation is simultaneously administered, these chimpanzees develop acute non-A, non-B hepatitis. The application of immunoglobulin cannot prevent the infection in this case (Spichtin H. -P. et al, Journal of Medical Virology 12, 215–226 (1983)).

The continuation of the above work was described by Eder et al (Viral Hepatitis and Liver Disease, 550–552; 1988); re-inoculation of the laboratory animals after two and four years resulted again non-A, non-B hepatitis.

In 1990, it was determined by the same group of researchers (Clin. Exp. Immunol. 81, 454–458, 1990) that multiple infusions of i.v. immunoglobulin in chimpanzees do not lead to immune elimination.

Work from Prince, A. M. et al (The Journal of Infectious Diseases, 165:438–43; 1992) describes that in the case of re-inoculation of chimpanzees with HCV, 59% of the test animals show seroconversion, 33% show HCV-associated hepatocellular ultrastructural changes and 26% develop hepatitis C. In sum, 74% of the experimental animals show at least one of the above mentioned symptoms after re-infection with HCV.

In the publication "Lack of protective Immunity Against Reinfection with Hepatitis C Virus" by Farci P. et al (Science, 250, 135–140; 1992), tests on 5 chimpanzees were described which demonstrated that HCV infection does not cause protective insanity against reinfection with homologous or heterologous strains. Hence, the authors showed doubt with respect to the development of effective vaccines against HCV.

The administration of immunoglobulin preparations alone is also known in the art, especially for substitution treatment of primary and secondary antibody deficiency conditions, such as the treatment of autoimmune and immune complex diseases such as idiopathic thrombocytopenic Purpura, adjuvant therapy bacterial infections, especially in acute bacterial infections, such as sepsis, meningitis or peritonitis or in chronic bacterial infections such as ostiomyelitis. In these cases, the preparation is administered intravenously. It is also known that intravenous gammaglobulin (ENDOBULIN®, a polyvalent immunoglobulin preparation in freeze dried, virus inactivated form) can be employed for immediate prophylaxis of viral diseases.

In the literature, experiments for determining the effect of neutralizing antibodies against coated viruses are described (Nature, vol. 321, 244–246 (1986)). The authors Gollins et al describe an in vitro model for illumination of the mechanism of action of a neutralizing antibody. In this connection, in vitro experiments with immunoglobulin-conditioned P388D1-cells and rabbit-IgG were carried out. It could be shown that a dose-dependent inhibition of the removal ("uncoating") of the virus envelope of the virus, and therewith the infection of the cells is prevented by the addition of immunoglobulin at 37° C. On page 245, right column, last paragraph, it is explained that it is to be assumed that a fusion between virus particles and endosomal membrane is prevented as a result of the presence of neutralizing antibodies. From this knowledge, the authors then derive how future neutralizing antibodies should be optimally constructed. The administration of a complex or conjugate of antigen and neutralizing antibody is not described in the above literature.

A so-called simultaneous vaccination is also known in the state of the art in which a viral vaccine for passive and active immunization respectively is administered in parallel, i.e. separately. As soon as a patient is exposed to a risk of infection, a hyper-immunoglobulin preparation for immediate neutralization of the pathogen and also a suitable antigen for stimulation of endogenous antibody production is normally administered in simultaneous vaccination. For example, an immunoglobulin preparation specific for the FSME virus (TBE virus of the western subtype) and, parallel thereto, a FSME vaccine based on the inactivated virus is successfully used post-exposure. For this, see Vaccine, Vol. 13(6), 759–762, 1995.

An object of the present invention is to provide a pharmaceutical composition which constitutes an improved vaccine. The pharmaceutical composition should especially cause enhanced immunity in humans and animals in order to create in case of highly mutating viruses, sufficient protection against the pathogen in this manner.

The above object is solved according to the invention by a pharmaceutical composition for prophylactic and/or therapeutic treatment of virus diseases which are caused by viruses with high mutation rates or viruses which exist in numerous genotypes or subtypes whereby the composition comprises a conjugate and/or complex of an enriched and/or purified virus and neutralizing antibodies. In other words, this means that the optionally pathogenic virus is administered in a neutralized form with antibody for the purpose of immunization.

The present invention is generally directed to the treatment of mammals, i.e. to the treatment of humans and animals.

Above all, viruses with high mutation rate are of particular importance as a target virus. There is still no vaccine for general prophylaxis and/or therapy against a viral disease which can he caused by most varied viral mutants. As soon as antibodies against an infective agent are formed, the risk of further modification of the virus already exists with these viruses, whereby the present antibodies can no longer function as neutralizing. Viruses with high mutation rate especially have the characteristic that they can repeatedly infect an organism in modified form. This so-called reinfection is observed above all with viruses which occur in most varied types, such as quasi-species, genotypes, subtypes and the like.

In particular, the target virus is one of the viruses transmittable through blood ("blood born"). These viruses can be isolated from body fluids, such as blood, serum, or plasma. In this connection, hepatitidae are to be named including HAV, HBV and HCV for example, but also the so-called AIDS viruses, such as HIV-1 and also parvovirus, cytomegalovirus, Epstein-Barr-virus.

Aside from the viruses isolatable from a body fluid which are partially distinguished by long incubation time and/or by relatively long viremia (duration of the viruses in the circulation), human pathogenic viruses are to be named which above all continuously appear in most varied forms.

For example, depending on their variability, various influenza A viruses appear whose infection can only be prevented by vaccines based on the corresponding inactivated types. Through the preparation according to the invention based on a neutralized influenza A virus, it is possible for the first time to globally use a type of the preparation for years, independent of the respectively occurring strains. The stability of the preparation also makes it possible to store these over a period of at least two years. Above all, one or a distinct mixture of influenza viruses which are present in activated form, are contained in the pharmaceutical compositions according to the invention. The activation of the virus is carried out for example by an enzyme treatment, especially with trypsin. Thereby, corresponding enzyme inhibitors, for example trypsin inhibitor, are also used, said inhibitors being depleted and/or separated in the course of the purification of the viruses.

For this purpose, purified and/or concentrated virus with suitable (specific) antibodies is treated in such a manner that the virus is not only neutralized, but in addition, does not lead to a productive infection in vivo. A productive infection means that despite the production of viruses there is no viral disease.

The pharmaceutical composition according to the invention is especially useable as a vaccine for prophylaxis against a virus disease. The prophylactic effect according to the invention is surprising in its extent in view of the simultaneous vaccine named in the state of the art.

Until now, it was not known in the state of the art to successfully use a conjugate and/or complex of an enriched and/or purified virus and neutralizing antibodies for the prophylaxis and/or therapy of virus diseases which are caused by viruses of high mutation rate or viruses which exist in numerous genotypes and/or subtypes. As indicated by the above-mentioned publication by Eder et al (1988) on infection of chimpanzees with an HCV infected Factor VIII preparation, simultaneous administration (parallel or simultaneous) with immunoglobulins could not inhibit infection with HCV and inflammation of the liver of the chimpanzees at first. In a recent infection experiment in which, according to the invention, purified HCV instead of HCV infected material was employed, the infection in the test animal could be modulated in view of reinfection. In this case, the test animal showed no morphological and biochemical signs of viral hepatitis. Of interest in this respect is that the immunoglobulin preparation used contained antibodies against the HCV-core and NS3-protein, i.e. antibodies against non-structural components of the virus. The administered dose thereby was very high at 100 m/kg, and it can be estimated that up to 500 mg IgG/kg can be administered.

The virus in the preparation according to the invention is present with the neutralizing antibody especially as a complex and/or as a conjugate. The association of the components exists as a result of the immunoaffinity but can also be formed as a covalent bond, optionally by a linker. This is also possible, for example, by a chemical crosslinking reaction or by the formation of sulfur bridges.

However, the complex bond can also exist as a result of electrostatic, hydrophobic or van der Waals' forces. In a further preferred embodiment, the antigen and the cell components are adsorbed and/or co-adsorbed to a solid support. The solid support can also be a lipid component, such as a liposome or phospholipid vesicle, for example. Thereby, it is of particular advantage to use an adjuvant as an adsorbent. Above all, an adjuvant based on mineral salts is suitable for this purpose. In particular, hydroxides of aluminum, iron and metals of the transition elements are suitable. These adjuvants not only stimulate the immune response, but also stabilize the immune complex. A more stable immune complex is necessary, above all, when the neutralized virus can become active again and possibly pathogenic perhaps by the separation of the neutralizing antibody. The addition of stabilizers permits the extension of the half-life in vitro and in vivo, whereby it is ensured that no unbound virus is present after administration of the pharmaceutical preparation according to the invention.

The stability of the pharmaceutical preparation according to the invention can be tested, for example, with an incubation experiment which is designed such that the incubation of the preparation according to the invention occurs under defined conditions in plasma or a correspondingly suitable medium. For example, the preparation can be incubated at a temperature of about 37° C. for a duration of up to several days and the possible dissociation of the immune complex by separation of the same and/or the determination of the optionally separated, i.e. unbound and optionally reactivated, viruses and/or antibodies, can be recorded.

As further adjuvants which also advantageously demonstrate a stabilizing effect, inorganic substances, such as diverse aluminum or iron compounds including the corresponding hydroxides and phosphates, oils, phospholipids, especially in vesicular fort, polypeptides or cytokines are also to be named.

The compositions according to the invention preferably contain flaviviruses or pestiviruses. According to a particularly preferred embodiment, which is not however a limiting one, the compositions according to the invention contain hepatitis C virus.

However, in principle, DNA and RNA viruses are used in the pharmaceutical compositions according to the invention. Thereby, the families of parvoviruses, papovaviruses, hepadnaviruses, adenoviruses, herpes viruses and poxviruses are to be mentioned as DNA viruses relevant for humans. Of particular significance among these families are; parvovirus B19, papovavirus JC, BK and SV40, papillomavirus, hepatitis B virus, adenovirus, herpes simplex 1 and 2 virus, varicella zoster, EBV, CMV and herpes 6 virus.

Among the relevant RNA viruses for humans and the diseases caused by them, the following are specifically mentioned: Rubella from the family togavirus, hepatitis C from the family flavivirus, hepatitis B from the family calcivirus, hepatitis A and Cox-sackie virus from the family picornavirus or the HTLV-I and II as well as HIV viruses from the group of retroviruses The reoviruses, for example, rotavirus or California-tick fever virus as well as hepatitis A (family of the picornaviruses) or hepatitis B (family of the caliciviruses) should be mentioned as examples of the uncoated viruses.

According to a preferred embodiment, the pharmaceutical compositions according to the invention contain-the neutralized virus in a purified form, especially in a highly concentrated or pure for.

The use of highly pure virus has the additional advantage that the various genotypes and/or subtypes can be separated. As a result, there can be a better neutralization effect of the antibody.

The purification of the viruses provided for the production of the composition according to the invention is preferably carried out by methods of chromatography, especially affinity chromatography or gel filtration, filtration, for example with nano-filters, adsorption treatments, precipitation, especially precipitation reactions with alcohol or tensides, or centrifugation, especially density-gradient centrifugation. Therewith, contaminating materials of the starting material are depleted above all to a pharmaceutically acceptable degree.

In the same manner as the virus is purified from a cultured medium, the neutralized virus which is present as a conjugate and/or as a complex can also be further purified with the same methods. Therewith, it should be ensured that non-neutralized viruses are separated.

According to a further embodiment of the invention, the virus relates to a recombinant virus produced in prokaryotes or eukaryotes. Furthermore, it is also possible to use virus fragments which have suitable antigens as the virus.

According to a further embodiment of the invention, the pharmaceutical compositions contain inactivated viruses aside from neutralized and/or neutralizable viruses.

The invention also relates to the exclusive use of inactivated viruses. In this case, the virus fraction used is preferably chemically or physically treated for inactivation of viruses.

In the case of inactivated viruses which are treated with chemical and/or physical methods, the inactivation can be carried out before the neutralization with the antibodies or on the immune complex and/or conjugate. Above all, a heat treatment, radiation treatment as well as a treatment with chemicals, such as solvents and/or detergents and chaotropic substances are suitable for this.

The antibodies used for the neutralization of the pharmaceutical compositions according to the invention are preferably isolated from plasma or a plasma fraction. However, it is additionally possible to isolate the antibodies from a cell culture.

According to a preferred embodiment, the antibodies obtained are present in a fraction which is pretreated for inactivation and/or depletion of possibly present viruses.

In the case of viruses transmittable through blood, antibodies which can be isolated from a hyper-immune and/or a serum from patients which came into contact with the pathogen are suitable above all for the production of the composition according to the invention. Preferable antibodies are polyclonal antibodies, especially human antibodies which can be mono-specific or poly-specific. With monospecific antibodies, a mixture of a multitude of antibodies is preferred.

It is preferred that the antibodies used for neutralizing the virus in the pharmaceutical compositions according to the invention are directed against more than one epitope. It is particularly preferred that the antibodies are directed against more than one viral antigen.

The antibodies used for neutralizing the pharmaceutical compositions according to the invention are directed against DNA as well as RNA viruses. Among these there are viruses with an envelope and/or to naked viruses. Thereby, it is preferred that the antibodies are directed against core proteins, i.e. non-structural proteins and/or against envelope proteins.

In any case, it is required that the selected antibodies neutralize the virus. The neutralization can be made possible as long as the virus no longer pathogenically functions but can productively infect the host.

This case of productive infection is defined in such a manner that the virus replicates and at least partially forms virus particles again without the host becoming ill. In the case of neutralization of the virus which allows the productive infection, it is preferred to use an excess of antibodies in the pharmaceutical composition according to the invention. Thereby, it is ensured that the virulence does not lead to an illness in the patient even with the replication of the virus in vivo.

A special embodiment relates to the neutralization of the virus, whereby, however, the productive infection is prevented. As preferred antibodies, protective antibodies are used which have the characteristics to protect an organism from a viral illness. The selection of the antibodies can be carried out in an exposure experiment ("challenge model"). After exposure of a model animal with the pathogen, it can be assessed whether the antibodies used protect against the outbreak of the disease or its consequences. Changes in physiological indicators such as antibody titer or other blood values and/or the death of the animal are among standards.

The antibodies used according to the invention are preferably native, intact antibodies which are essentially free from immunoglobulin aggregates. An inadmissibly high unspecific anti-complementary activity is prevented therewith. It bas been shown that antibody fragments are less suitable because the free, i.e. unbound, Fc part of the antibody contributes essentially to the immune response.

According to a preferred embodiment, the composition according to the invention may comprise further substances which produce an improvement with respect to neutralization of the virus or enhancement of the immune response. Hence, the composition according to the invention may comprise complement for example.

According to a preferred embodiment, the composition according to the invention is suitable for intravenous administration. Therewith, this preparation has characteristics which are defined for intravenously acceptable immunoglobulin preparations according to the guidelines of the German pharmacopia DAB 1: (3rd supplement 1994) "Immunoglobulin vom Menschen zur intravenösen Anwendung". A further embodiment relates to a suitable composition which comprises antibodies which are capable of being orally administered or mucosally assimilated. Above all, IgA which-are known to be able to be assimilated over the mucosa are among these.

Furthermore, those antibodies are also defied as capable of being mucosally administered which respond to the antibody composition from colostrum, for example.

Aside from the intravenous and oral administration possibility of the composition according to the invention, further systemic or local modes of administration are possible. Among others, a corresponding vaccine can be administered intramuscularly or subcutaneously, rectally, nasally or intracavity.

Incidently, the doses of IgG to be administered can be in the range of the upper value of the dosages which are usually given for example in substitution treatment of primary and secondary antibody deficiency conditions. In these cases, up to 1000 mg/kg body weight are administered within 14 days. Medium dosages are equivalent to those used in therapeutic plasma exchange; here, 200 mg/kg body weight are administered as a rule, however the dosages of intravenous gammaglobulin can also be increased in this case up to 1,000 mg/kg body weight/day.

Lower values with respect to the administration of IgG can correspond to those of the immediate prophylaxis of viral infections the dosages are distinctly lower, for example, 10 to 20 mg/kg body weight for hepatitis A and 50 mg/kg body weight for measles and varicella.

According to the state of the examinations, it is preferred to administer a minimal dose of 100 mg/kg body weight and, particularly preferred, a dose 2- to 5-fold thereof, namely 200 to 500 mg/kg body weight.

It is preferred that the antibodies in the pharmaceutical composition according to the invention are included in a high concentration so that a highly dosed administration is possible.

With respect to a preferred ratio of virus to antibody in the pharmaceutical preparation according to the invention, it is desired to use a multiple of the amount of antibody needed for neutralization of the virus in order to take into full account the safety efforts. In this connection, however, the antibody dose should not be so high that the object, namely the immunization, is prevented.

The animal experiments on chimpanzees carried out according to the invention have clearly shown that a mitigation of the course of disease following an infection with a virus can be obtained by the administration of the claimed pharmaceutical preparation. The preparations according to the invention lead to an improvement of liver histology and, therewith, to the improvement of liver function of patients infected with the virus.

The present invention is not restricted to the mitigation of the course of disease following HCV infection, but instead relates in toto to pharmaceutical preparations which are suitable to generally cause enhanced immunity of the host against the pathogen in viral infections. The pharmaceutical preparation according to the invention are especially suitable as vaccines against viruses which steadily change their phenotype through frequent mutations.

A limited protection can be of advantage above al with chronic illnesses. In any case, it was-observed that a pharmaceutical composition according to.-the invention did not lead to a complete protection against hepatitis C in a chimpanzee, but the illness was not as serious as expected. Thereby, it was observed that the liver function values were improved in comparison to an untreated chimpanzee. No increase of the liver-specific enzymes ALT (amino-alanine transferase) in serum resulted in contrast to untreated chimpanzees. It is known of hepatotropic viruses that these lead to liver function changes in the sense of an increase of the liver enzymes in serum (ALT=amino-alanine transferase, AST=amino-aspartate transferase) in infections in the absence of protective antibodies. The increase of the liver enzyme ALT is generally an expression of necrosis of the hepatocytes. In chronic infections, month-long to year-long damage of the hepatocytes can result through the hepatitis virus and persistence of the increased serum liver enzymes can result.

Subsequently, an alteration of the liver tissue can also result whereby formation of liver cirrhosis and appearance of a liver carcinoma can also result with hepatitis B for example. With hepatitis C, this phase accompanies a slight increase of the ALT-values, but the chronicity is considerably higher than with hepatitis B. Whether hepatitis C plays a considerable as one of the causes of the liver carcinoma is not yet determined. The magnitude of the chronicity of hepatitidae could also depend on the degree of the mutation rate of these viruses with lacking antibody formation and/or be caused by the protracted formation of specific antibodies. The chronicity can also be triggered by reinfection with other genotypes or subtypes of the same virus. A limited infection and/or the prevention of the chronicity is already to be seen as a success.

Additionally, the invention comprises a kit for producing pharmaceutical compositions, wherein this kit comprises (a) the purified virus and/or the virus concentrated in a fraction and (b) the antibodies neutralizing the virus.

Moreover, the invention comprises the use of a virus neutralized with antibody for the production of a pharmaceutical preparation which is suitable for mitigating the course of disease following infection with the virus. An improvement of liver histology is especially obtained according to the invention which in practice improves the liver function of the patient.

The invention is illustrated in detail by means of the following example:

The following example illustrates the experiment with hepatotropic viruses. The respective target organ must be examined and judged in case of other viruses.

Materials and methods:

1. Experimental animals:

The chimpanzee is the suitable animal model in order to test the protective effect of a prophylactic therapy with the pharmaceutical composition according to the invention (Tabor et al, J. Med. Primatol. 12:305–318, (1983)). However, for some viruses, other primates can also be used (for example, cynomolgus apes for hepatitis B).

Eight naive chimpanzees (pan troglodytes) a used for this experiment. The chimpanzees must be healthy, must not have any marker of hepatitis B, C and D, and cannot have been in any experiment with human material, for example, factor VIII concentrate or vaccines against the virus used in the pharmaceutical composition (abbreviated PC). The chimpanzees should be held in an animal facility corresponding to biosafety level 2. Two of the eight chimpanzees are control animals and do not receive PC. The other chimpanzees repeatedly receive the PC intravenously, intramuscularly, or sub- or intracutaneously even in intervals of four weeks or six months (two chimpanzees each if possible). All blood samples are taken and liver biopsies are performed under ketamine narcosis.

2. Hepatitis serology:

In a prephase to the experiment which lasts at least four months, the chimpanzees are examined for hepatitis B, C and D markets. The following tests must be negative not only because of the virus to be expected but also because of possible interference:

Hepatitis B surface antigen

Hepatitis B surface antibody

Hepatitis B core antibody (IgG and IgM)

Hepatitis B antigen and antibody

HBV DNA by means of PCR

Hepatitis C antibody

Hepatitis C riba test

HCV RNA by means of PCR

Hepatitis D antibody

Hepatitis D antigen.

If other preparations, for example against hepatitis B, are to be tested, all markers against this virus—hepatitis B—must also be negative. All tests must be subjected to an internal and if possible external quality control. All tests are carried out in two week intervals.

3. Liver enzymes:

For examination of liver function and/or as an indicator of an acute inflammation, both the enzymes alanine aminotransferase (ALT EC 2.6.1.2) and gamma-glutamyltransferase (G-GT EC 2.3.2.2.) are used. Liver enzymes arae tested weekly. Healthy chimpanzees have an ALT-concentration in serum which corresponds to that of human beings (Eder et al, The Role of the Chimpanzee in Research, Symp., Vienna, 156–165, (1994)). Measurement is conducted according to the recommendations of the "German Society for Clinical Chemistry" (1972). The ALT value in serum is elevated when damage of the hepatocytes results as a consequence of increased permeability of the cell membrane or cell necrosis (Thefield et al, Dtsch. med. Wschr. 994:343–351 (1974), Wallnoefer et al, in Synopsis der Leberkrankheiten, Thieme Verlag, Stuttgart, (1974), Schmidt et al, Laboratory and Clinical Science, New York, 411–487 (1983), Wuest H, Klin. Gastroenterologie in 2 Bänden, Thieme Verlag, Stuttgart, (1984)). It is known that a distinct increase of the ALT values appears in 70 to 100% of the cases by inoculation with hepatitis B virus in chimpanzees (Tabor et al 1983). Before discovery of the hepatitis C virus, an ALT increase over 2.5-fold of the upper normal value was considered as indicative for hepatitis C. In hepatitis which is caused by other viruses, an increase of ALT was also found (Eder, ALT- and C-GT increase in EBV hepatitis chimpanzees, unpublished results). On the other hand, the enzyme G-GT is detectable mainly in the membrane of those cells which play a high absorptive or secretory role (namely, liver, kidney and pancreas). The biological role of G-GT is not yet fully explained. In contrast to the enzyme ALT, G-GT is membrane bound and detectable in the bile duct and Kupffer cells (Rosalik et al, Clin. Chem. Acta 39:41–47 (1972), Rosalik et al, Clin. Chem. 7:53–107 (1975); Valenza et al, J. Med. Primatol. 14:350–315 (1985); Weill et al, Gamma-glutamyltransferases: advances in biomedical pharmacology, 3rd series, Masson, Paris, page 195–198 1982)). G-GT is found in the-parenchyma cells in only a small percentage. Because G-GT is actively secreted into serum, this enzyme is the most sensitive indicator for damage to the cell membrane and can successfully be used for detection of hepatitis. With an increase in G-GT, an obstruction of the biliary tract and consumption and/or misuse of alcohol must be excluded. Our own, unpublished examinations have shown that G-GT is a better indicator than ALT for the detection of liver inflammation. Determination is conducted according to the recommendations of the German Society for Clinical Chemistry (Persijn et al, J. Clin. Chem. Clin. Biochem. 149, 421–427 (1976). The normal values of the chimpanzees correspond to those of human beings.

4. Examination of liver tissue:

The animals are liver-punctured in the pre-experimental and experimental phase at intervals of 2 weeks. A liver biopsy needle according to Menghini or another commercially available system is used. The removed liver tissue samples are fixed in paraformaldehyde for light microscope examination, shock frozen in liquid nitrogen for the immunohistochemical examination and fixed in glutaraldehyde for the electron microscope examination. All tests are carried out in coded form. The samples intended for light microscopy are routinely stained with haematoxyllin eosin, PAS and Mallory. Polyclonal and monoclonal antibodies which react with one or more antigens of the virus are used immunohistochemically. The antibodies are conjugated either with fluorescein or biotin.

All results of the chimpanzees' liver biopsy findings must be normal in the prephase. A low-grade, non-specific reactive hepatitis can be tolerated because this is also found sometimes in totally healthy chimpanzees. The results during the experimental phase are graduated according to the human score system (scale 0 to 18) (Ishak at al, J. Hepatol. 22:696–699 (1985)). Ultrastructural chances as they are described for viral infections, for example hepatitis C, are especially judged in the electron microscope experiments (Pfeifer et al, Virchow Archive B Cell Pathol. 20:617–627 (1980), Schaff et al, Virchow Archive B Cell Pathol. 45:301–312 (1984), Schaff at al, J. Ultrastr. Path. 14:303–309 (1990)).

5. Pharmaceutical composition:

The PC already contains the immunoglobulin preparation or the latter is administered separate to a preparation which contains the virus that does not lead to a productive infection.

In the experiments regarding Hepatitis C, the virus preparation can comprise several genotypes as well as a mixture of several subtypes.

The amount of virus used corresponds to a concentration of productive virus of $10^3$ CID 50/ml. The gammaglobulin dose which is intravenously administered is 100 mg/kg body weight.

Experimental method:

Both control animals do not receive the pharmaceutical preparation. All animals are subject to a challenge experiment after reaching suitable antibody formation in the experimental animals. The challenge dose corresponds to an average concentration of virus which is fond to be productive in the case of disease, for example hepatitis C $10^{1.5}$ CID/ml.

Results:

In both control chimpanzees, which did not receive any pharmaceutical preparation, a virus infection after suitable incubation time, an increase in G-GT with and without ALT increase as well as viral genome equivalents could be detected after the challenge. This demonstrates the effectiveness of the challenge material.

After the dose of PC, the passively administered antibody which was present in excess can be detected in the remaining experimental animals corresponding to its half-life. After the challenge, the chimpanzee that received the lowest dose of PC showed the longest half-life of the viral antigen administered with the challenge material.

In the immunized chimpanzees, no ultrastructural changes of the liver relating to a viral infection could be detected byelectron microscopy and no acute hepatitis could be detected by a light microscope. There was no increase of the liver enzymes ALT and G-GT as a result post-challenge; virus could neither be isolated from serum or liver tissue nor detected consecutively by means of PCR.

We claim:

1. A composition for treating a hepatitis C virus (HCV) infection in a mammal, comprising inactivated HCV bound to neutralizing human HCV antibodies, wherein the antibodies are against at least one protein selected from the group consisting of HCV-core protein and NS3-protein.

2. The composition according to claim 1, wherein an administered dose of antibodies is at least 100 mg per kg body weight.

3. The composition according to claim 1, wherein an administered dose of antibodies is no more than 1000 mg per kg body weight per day.

4. A method of mitigating the course of a HCV infection, comprising administering to a mammal suffering from HCV infection a composition comprising inactivated HCV bound to neutralizing human HCV antibodies, wherein the antibodies are against at least one protein selected from the group consisting of HCV-core protein and NS3-protein.

5. The method according to claim 4, wherein the administered dose of antibodies is at least 100 mg per kg body weight.

6. The composition according to claim 4, wherein the administered dose of antibodies is no more than 1000 mg per kg body weight per day.

7. A method of improving the liver function of a mammal having HCV infection, comprising administering to the mammal a composition comprising a inactivated HCV bound to neutralizing human HCV antibodies, wherein the antibodies are against at least one protein selected from the group consisting of HCV-core protein and NS3-protein.

8. The method according to claim 7, wherein the administered dose of antibodies is at least 100 mg per kg body weight.

9. The composition according to claim 7, wherein the administered dose of antibodies is no more than 1000 mg per kg body weight per day.

* * * * *